US012569374B2

(12) United States Patent
Bäck

(10) Patent No.: US 12,569,374 B2
(45) Date of Patent: Mar. 10, 2026

(54) ABSORBENT ARTICLE HAVING CHANNELS

(71) Applicant: Essity Hygiene and Health Aktiebolag, Gothenburg (SE)

(72) Inventor: Lucas Bäck, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 319 days.

(21) Appl. No.: 18/557,698

(22) PCT Filed: Feb. 28, 2022

(86) PCT No.: PCT/EP2022/054913
§ 371 (c)(1),
(2) Date: Oct. 27, 2023

(87) PCT Pub. No.: WO2022/258234
PCT Pub. Date: Dec. 15, 2022

(65) Prior Publication Data
US 2024/0238132 A1     Jul. 18, 2024

(30) Foreign Application Priority Data

Jun. 9, 2021    (WO) ................. PCT/EP2021/065376

(51) Int. Cl.
*A61F 13/49*     (2006.01)
*A61F 13/511*     (2006.01)
(Continued)

(52) U.S. Cl.
CPC ........ *A61F 13/49* (2013.01); *A61F 13/51108* (2013.01); *A61F 13/5323* (2013.01);
(Continued)

(58) Field of Classification Search
CPC .................................................. A61F 13/494
See application file for complete search history.

(56) References Cited

U.S. PATENT DOCUMENTS 12,472,111 B2 * 11/2025 Bianchi ................. A61F 13/532
2006/0064069 A1     3/2006 Rajala et al.
(Continued)

FOREIGN PATENT DOCUMENTS

CL     2016003034 A1     4/2017
CL     2020000636 A1     9/2020
(Continued)

OTHER PUBLICATIONS

International Search Report (PCT/ISA/210) and Written Opinion (PCT/ISA/237) mailed on Jun. 24, 2022, by the European Patent Office as the International Searching Authority for International Application No. PCT/EP2022/054913. (14 pages).
(Continued)

*Primary Examiner* — Susan S Su
*Assistant Examiner* — Ted Yang
(74) *Attorney, Agent, or Firm* — BUCHANAN INGERSOLL & ROONEY PC

(57) ABSTRACT

An absorbent article comprising an absorbent core being enclosed by a liquid-permeable core cover comprising an upper core cover layer and a lower core cover layer and having a longitudinal center line. The absorbent core has a pair of longitudinally extending side edges and a pair of transversely extending end edges. The core cover layers are connected inside seals extending along the side edges of the absorbent core. The absorbent core comprises one or more longitudinally extending channels arranged at a distance from the side seals, each of the one or more channels being free or substantially free from absorbent material and having a channel seal extending therein. The channel seal joins the upper and lower core cover layers of the core cover within the channel, with a seal strength of the channel seal being higher than a seal strength of each of the first and the second side seals of the absorbent core.

21 Claims, 5 Drawing Sheets

(51) Int. Cl.
    *A61F 13/53*          (2006.01)
    *A61F 13/532*       (2006.01)

(52) U.S. Cl.
    CPC ............... *A61F 2013/49074* (2013.01); *A61F 2013/5307* (2013.01)

(56) References Cited

U.S. PATENT DOCUMENTS

| | | | |
|---|---|---|---|
| 2017/0079858 A1* | 3/2017 | Willhaus | A61F 13/532 |
| 2017/0312146 A1 | 11/2017 | Bianchi et al. | |
| 2019/0117476 A1 | 4/2019 | Bianchi | |
| 2019/0117477 A1* | 4/2019 | Bianchi | A61F 13/4704 |
| 2020/0276059 A1 | 9/2020 | Smet et al. | |
| 2020/0360199 A1* | 11/2020 | Stiehl | A61F 13/53409 |
| 2021/0093489 A1* | 4/2021 | Manabe | A61F 13/536 |

FOREIGN PATENT DOCUMENTS

| | | | |
|---|---|---|---|
| EP | 1974705 A1 | 10/2008 | |
| EP | 2586412 A1 | 5/2013 | |
| EP | 2870951 A1 | 5/2015 | |
| EP | 2949299 A1 | 12/2015 | |
| EP | 3473223 A1 | 4/2019 | |
| JP | 2014515981 A | 7/2014 | |
| JP | 2018528015 A | 9/2018 | |
| WO | 2004078082 A1 | 9/2004 | |
| WO | 2012170778 A1 | 12/2012 | |
| WO | 2014007043 A1 | 1/2014 | |
| WO | 2017053036 A1 | 3/2017 | |
| WO | 2019048397 A1 | 3/2019 | |
| WO | 2019125231 A1 | 6/2019 | |
| WO | 2021015656 A1 | 1/2021 | |

OTHER PUBLICATIONS

Office Action (Notice of Reasons for Rejection) issued on Jul. 22, 2025, by the Japanese Patent Office in corresponding Japanese Patent Application No. 2023-575923, and an English Translation of the Office Action. (15 pages).

Office Action issued on Jun. 18, 2025, by the Chilean Patent Office in corresponding Chilean Patent Application No. 2023-03675, and a machine English Translation of the Office Action. (36 pages).

Office Action issued on Nov. 24, 2025, by the Chilean Patent Office in corresponding Chilean Patent Application No. 202303675, and an English Translation of the Office Action. (21 pages).

* cited by examiner

ABSORBENT ARTICLE HAVING CHANNELS

TECHNICAL FIELD

The present disclosure pertains to an absorbent article comprising an absorbent core being enclosed by a liquid-permeable core cover comprising an upper core cover layer and a lower core cover layer. The upper core cover layer and the lower core cover layer are connected in a first side seal extending along a first side edge of the absorbent core and in a second side seal extending along a second side edge of the absorbent core. The absorbent core comprises one or more channels extending in the longitudinal direction at a distance from each of the first side seal and the second side seal, each of the one or more channels having a channel seal extending therein and joining the upper and lower layers of the core cover within the channel.

BACKGROUND

In disposable absorbent articles, such as baby diapers and other articles for absorption of body fluids such as pant-type absorbent garments, incontinence protectors and sanitary napkins, there is a conflict between the requirement of sufficient absorption capacity and leakage security on the one hand and wearer comfort and discretion on the other hand. Accordingly, there is a demand for highly absorbent articles which are non-bulky and flexible, and which conform well to the body of a wearer. It is highly desirable that the wearer does not feel restricted or uncomfortable when wearing the absorbent article while still being confident that the article is efficient in preventing leakage. For adult user's it is particularly important that a pant-type garment resembles ordinary underwear as closely as possible and can be inconspicuously worn under normal tightfitting clothing. To provide sufficient absorption capacity while offering thin absorbent articles, a large proportion of the absorbent material may be what is commonly known as superabsorbent material or merely "superabsorbents". The superabsorbents may be combined with absorbent fibers, predominantly cellulose pulp fibers, creating a fibrous network which contributes to distribute liquid in the absorbent core and to retain particulate superabsorbent material in the core.

Superabsorbents are polymeric materials usually incorporated in absorbent articles in the form of fibers, particles, or granules. Superabsorbents can absorb many times their own weight of fluid upon swelling and formation of a hydrogel. Absorbent articles which contain a large amount of superabsorbent material have been found to lose their initial flexibility and wearer comfort as they absorb liquid and swell. High-impact areas of an absorbent article, such as the crotch portion of a diaper which contains a large amount of absorbent material distributed over a relatively small area may grow thick and become stiff as the article absorbs liquid. Moreover, it is a concern in disposable absorbent articles that the available absorption capacity of the absorbent material may be utilized as fully as possible, to keep material consumption at a minimum when producing the absorbent articles. It is therefore desirable that the full absorbent capacity of the superabsorbents can be utilized. In absorbent cores having a high content of superabsorbent material, such as 50% superabsorbent material or more and a relatively low amount of cellulose pulp fibers or no cellulose fibers, it has been proposed to provide additional stabilization of the absorbent core.

In WO2019/125231 A1 it has been suggested to stabilize an absorbent core and counteract sagging in the crotch portion of an absorbent article by forming two longitudinally extending channel sealings in the absorbent core. The absorbent core is enclosed within a core cover and the channel sealings join an upper side of the core cover with a lower side of the core cover and are arranged such that they divide the absorbent core into a center segment and two side segments. When the absorbent material in the absorbent core absorbs body fluids and swells, the core cover acts as swelling restriction means by limiting the swelling room for the absorption material in the different segments. Thereby, the expanding absorption material exerts outward pressure on the core cover resulting in an increase in stiffness of the absorbent core in the crotch portion of the absorbent article. Particularly high stiffness may thereby be achieved in the center segment of the absorbent core, between the two channel sealings.

SUMMARY

The present disclosure is based on the insight that an absorbent article having improved fit, body conformance and wearer comfort as well as good absorbency and leakage security, may be achieved at least in part by the features of claim 1. Variations of the disclosure are set out in the dependent claims and in the following description.

The absorbent articles referred to herein may be wearable disposable absorbent articles, for example in the form of open diapers, pant diapers, belted diapers, incontinence garments, feminine hygiene garments and the like, as well as disposable absorbent inserts, e.g., incontinence shields or sanitary napkins, which are worn inside a support garment, such as a support pant or ordinary underwear.

The articles are used to absorb, distribute, and store various types of body exudates while providing a high level of comfort and a sense of dryness to the wearer during wearing.

The present disclosure is directed to an absorbent article comprising an absorbent core, the absorbent core comprising absorbent material. The absorbent core is enclosed by a liquid-permeable core cover, the core cover comprising an upper core cover layer and a lower core cover layer. The article and the absorbent core have a longitudinal direction and a transverse direction perpendicular to the longitudinal direction, with a longitudinal center line extending in the longitudinal direction. The absorbent core has a first side edge and a second side edge, the first side edge and the second side edge of the absorbent core having a main extension in the longitudinal direction, and a first end edge and a second end edge, the first end edge and the second end edge having a main extension in the transverse direction. The upper core cover layer and the lower core cover layer are connected in a first side seal extending along the first side edge of the absorbent core and in a second side seal extending along the second side edge of the absorbent core. The absorbent core comprises one or more channels extending in the longitudinal direction at a distance from each of the first side seal and the second side seal. Each of the one or more channels is free or substantially free from absorbent material and has a channel seal extending therein, the channel seal joining the upper and lower layers of the core cover within the channel, wherein a seal strength of the channel seal is higher than a seal strength of each of the first and the second side seals of the absorbent core.

The channel seal or channel seals prevent separation of the upper and lower core cover layers and thereby restricts swelling in the thickness direction of the absorbent core in the vicinity of the channels. The channel seals are preferably permanent seals, or at least a major part of each channel seal is a permanent seal which does not break under normal use and handling of the absorbent article. A permanent seal resists the forces arising from swelling absorbent material in the absorbent core and remains intact throughout use of the absorbent article. The side seals are breakable seals which break under influence of the forces exerted on the side seals as the absorbent material in the absorbent core absorbs fluid and expands. The breakable side seals together with the channel seals promote expansion of the absorbent material predominantly in the lateral or transverse direction of the absorbent core and the absorbent article.

The seal strength of the channel seal or channel seals may be 2.5 N/25 millimeter or more, such as 3 N/25 millimeter or more and the seal strength of the first and the second side seals may be 2.0 N/25 millimeter or less, such as 1.5 N/25 millimeter or less, as measured according to the test method disclosed herein.

There is no upper limit for the seal strength of the permanent channel seal or channel seals as the only require-ment for a channel seal is that it does not break under the pressure which may be exerted on the seal during normal use. For the breakable first and second side seals, it may be sufficient that the seal strength is sufficiently high to main-tain at least some integrity of the side seals while the absorbent material between the channel seals and the side seals remains dry. In some instances, it may be sufficient that the upper and lower core cover layers are kept together merely by frictional forces in parts of the core cover extend-ing laterally beyond the absorbent core.

The side seals may be partly breakable seals and partly permanent seals. A part of a side seal located adjacent the side edge of the core may be breakable while an outer part of the side seal which is located at a distance from the side edge may be a permanent seal which stops the core cover layers from fully separating from each other.

The side seals and the channel seal(s) may be adhesive seals, weld seals, or any combination of adhesive seals and weld seals. The seals may be formed as continuous bond lines or may be formed by discrete bond elements arranged along the seals.

The side seals may be seals having very low integrity, such as mechanical seals having been formed e.g., by needling or embossing the upper and lower core layers together.

The first side seal, the second side seal and each channel seal may be adhesive seals. The seal strength of the seals may be controlled by varying the basis weight of the applied adhesive in the seals. Accordingly, a basis weight of adhe-sive in each channel seal may be higher than a basis weight of adhesive in each of the first side seal and the second side seal. The basis weight of adhesive may also be varied along the seals. In a channel seal, the basis weight of the applied adhesive may be higher in a longitudinally central part of the channel seal than at one or both end parts of the channel seal, allowing the end parts of the channel seal to break upon swelling of the absorbent material while the central part of the channel seal remains intact. The permanently sealed part of the channel seal or channel seals may extend in a portion of the absorbent core which is arranged on a non-elastic crotch material, such as on a non-elastic crotch panel or on a non-elastic crotch part of an outer cover of the absorbent article such as an absorbent pant article or an absorbent open diaper. The breakable end parts of the channel seal or channel seals may extend in portions of the absorbent core which are arranged on elastic front and rear body panels of the absorbent article.

In an absorbent article as disclosed herein, the basis weight of adhesive in each channel seal may be 3 $g/m^2$ or more, such as in the range of from 3 $g/m^2$ to 15 $g/m^2$. The basis weight of adhesive in each side seal may be 5 $g/m^2$ or less, such as in the range of from 0.5 $g/m^2$ to 5 $g/m^2$.

For thermo-seals and weld seals, such as ultrasonically welded seals, the seal strength may be controlled by varying parameters such as sealing temperature, energy supply, sealing time and sealing pressure and/or by varying the sealing pattern.

The core cover may be formed from a single continuous cover material being wrapped around the absorbent core, the first side edge and the second side edge of the absorbent core being arranged inside a corresponding first side fold and a second side fold in the continuous cover material, wherein the first and second side seals are arranged laterally inward of the corresponding first and second side folds.

Alternatively, the upper core cover layer and the lower core cover layer may be separate core cover layers, sand-wiching the absorbent core therebetween.

In an absorbent article as disclosed herein, the absorbent article may comprise a liquid permeable topsheet and a liquid barrier layer, the absorbent core being arranged between the liquid permeable topsheet and the liquid barrier layer. The liquid permeable topsheet and the liquid barrier layer are provided in addition to the upper core cover layer and the lower core cover layer, with the upper core cover layer facing the liquid permeable topsheet and the lower core cover layer facing the liquid barrier layer.

The liquid permeable topsheet, the liquid barrier layer and the absorbent core with the core cover may be part of or constitute an absorbent assembly or "core pack" which is produced as a separate unit and subsequently attached to front and back panels of an open-type or pant-type wearable article or to an outer cover of an open-type or pant-type wearable article.

The absorbent core of an absorbent article as disclosed herein may comprise superabsorbent material, preferably from 5% by weight to 80% by weight of superabsorbent material, such as from 30% by weight to 80% by weight of superabsorbent material, at least in a part of the absorbent core which is arranged in a crotch portion of the absorbent article. Accordingly, the superabsorbent content may be lower in a front end part and/or in a rear end part of the absorbent core than in a central part of the absorbent core.

The superabsorbent material is a polymeric material and may be in the form of particles, granules fibers, flakes, etc.

The absorbent core may comprise a mixture of cellulose pulp fibers and superabsorbent material.

A high amount of superabsorbent material in the absor-bent core, makes it possible to produce absorbent articles which are thin and discrete while offering high absorbent capacity and an ability of chemically binding absorbed fluid which results in an absorbent article having high leakage security and a dry inner surface even after having absorbed a large amount of fluid. The thin, superabsorbent-containing articles further has pre-use advantages, as they occupy less space for packaging, transport, and storage, as well as on a store shelf.

The one or more channels may be constituted by two channels extending spaced apart and symmetrically arranged on each side of the longitudinal center line, between the longitudinal center line and a corresponding one of the first side seal and the second side seal.

The length of each of the one or more channels in the longitudinal direction of the article may be in the range of from 50 millimeter to 500 millimeter, such as from 75 millimeter to 400 millimeter, from 100 millimeter to 300 millimeter or from 150 millimeter to 200 millimeter.

The absorbent core may have any suitable shape in the plane defined by the longitudinal direction and the transverse direction, such as an hourglass shape or a T-shape.

The absorbent core may comprise two or more parts having different absorption capacity. The absorbent core may be a three-dimensionally shaped, profiled core with a central part of the absorbent core being arranged between a first end part of the absorbent core and a second end part of the absorbent core, as seen in the longitudinal direction, the central part of the absorbent core having a greater thickness than a thickness of the first end part and a greater thickness than a thickness of the second end part.

The central part of the absorbent core may have a uniform first thickness, the first end part may have a uniform second thickness and the second end part may have a uniform third thickness. The first thickness may be equal to the second thickness. The central part of the absorbent core may be delimited from each of the first end part and the second end part by a corresponding first transition zone and a second transition zone.

The first end part may be a front end part and the first transition zone may be a front transition zone having an extension in the longitudinal direction of from 5 millimeter to 30 millimeter, such as from 10 millimeter to 20 millimeter, and wherein the second end part is a rear end part and the second transition zone is a rear transition zone having an extension in the longitudinal direction of from 20 millimeter to 80 millimeter, such as from 30 millimeter to 60 millimeter. The thickness of the absorbent core preferably changes linearly in the transition zones between the end parts and the central part.

A ratio between the thickness of the central part of the absorbent core and the thickness of the first end part may be in the range of from 4 to 1.5 and a ratio between the thickness of the central part of the absorbent core and the thickness of the second end part may be in the range of from 4 to 1.5.

The end parts may have equal thickness. However, end parts having different thickness are also conceivable for the absorbent articles as disclosed herein. A front end part may have a greater thickness than a rear end part.

The length of the absorbent core in an absorbent article as disclosed herein is determined as the distance between a point on the first end edge of the absorbent core where the first end edge intersects with the longitudinal center line and a point on the second end edge of the absorbent core where the second end edge intersects with the longitudinal center line, the length of the absorbent core being in the range of from 300 millimeter to 700 millimeter, such as from 350 millimeter to 600 millimeter or from 400 millimeter to 500 millimeter.

In an absorbent core having a thickened central part, the thickened central part may have a length in the order of from 30% to 70% of the length of the absorbent core, such as in the order of from 40% to 60% of the length of the absorbent core or from 45% to 55% of the length of the absorbent core. The length of the thickened central part may be approximately half the length of the absorbent core.

The absorbent core in an absorbent article as disclosed herein may have any planar shape, such as a rectangular shape, a T-shape, or an hourglass shape.

Hourglass shapes include all configurations of the core where the end parts are wider than the central part. A planar shape with the central part being narrower than the end parts may be preferred over rectangular shapes, as a narrow central part may fit more comfortably in the crotch of a wearer. Moreover, a narrow central part of the absorbent core may allow greater transverse expansion of the core during use of the absorbent article without causing discomfort.

An absorbent article as disclosed herein, may comprise a three-dimensionally shaped core with a thicker central part and thinner end parts, the core being enclosed by a core cover comprising an upper layer and a lower layer. The upper and lower layers may be formed from a single web material or from two web materials. The cover material may be a nonwoven material. The core has one or more sealed channels arranged therein, such as two sealed channels being symmetrically arranged on each side of a longitudinally extending center line of the article. The upper and lower layers of the core cover are bonded to each other with channel seals which are arranged in the one or more channels. The upper and lower layers are also bonded to each other by side seals extending along the side edges of the absorbent core. The one or more channels are free from absorbent material, implying that the upper and lower layers of the core cover are directly bonded to each other in the channel seals. The channel seals are permanent seals, as defined herein and the side seals are breakable seals, as defined herein. The side seals will break under influence of the expanding forces exerted on the side seals by the absorbent material in the core, as the absorbent material absorbs fluid and swells, thereby allowing the absorbent core to expand in the transverse direction of the absorbent article. Thus, the breaking side seals provides additional expansion room along the side edges of the absorbent core and counteract unwanted thickening and stiffening of the side portions of the absorbent core. The absorbent core may also be shaped in the plane, such as having an hour-glass shape with the central part of the absorbent core being narrower than the first and second end parts.

In a three-dimensionally shaped absorbent core as disclosed herein, the thinner end parts may have a uniform or substantially uniform thickness, and the thicker central part may have a uniform or substantially uniform thickness. Transition zones may be arranged between the thicker central part and the thinner end parts, the thickness of the absorbent core preferably diminishing linearly or substantially linearly from the central part to the end parts within the transition zones. The end parts may be a designated front end part and a designated rear end part, with the rear end part having a greater extension in the longitudinal direction of the absorbent article than the front end part. The rear transition zone may have a greater extension in the longitudinal direction of the absorbent article than the front transition zone, as disclosed herein.

As disclosed herein, the core cover may be formed by a separate upper core cover layer and a separate lower core cover layer forming the lower side of the core cover, the upper and lower core cover layers together enclosing the absorbent component and being sealed together at least along the side edges of the absorbent core. Preferably, the upper and lower core cover layers are sealed together along the full periphery of the absorbent core.

When the core cover is formed from a single material layer, the single material layer may be wrapped around the absorbent core or may be formed as a tubular structure into which the absorbent component is inserted. The core cover is sealed at least in the longitudinal direction, which means that the ends of the core cover may be left open. Preferably, the core cover is sealed so that the absorbent core is completely enclosed inside the core cover. Furthermore, the core cover may be made from more than two material layers.

The basis weight of the core cover materials as used herein may be in the range of from 5 g/m² to 20 g/m². The core cover material may be made of thermoplastic polymer material, such as polyolefin, polyesters, polyamide and combinations thereof. The core cover material may be a nonwoven material, a perforated plastic film, a netting, etc. A nonwoven layer may be formed by any of a variety of different processes, as known in the art, such as spunbonding, airlaying, meltblowing or bonded carded web formation processes. The nonwoven layer may be made of co-formed lamina of nonwoven materials such as an SMS (spunbond/meltblown/spunbond) nonwoven material an SMMS nonwoven material (spunbond/meltblown/meltblown/spunbond) or an SS (spunbond/spunbond) nonwoven material. The thermoplastic polymer materials in the nonwoven layer may be polypropylene or bicomponent fibers of polypropylene and polyethylene, or of a combination of such materials.

The absorbent core may be constituted by one single absorbent component layer.

Absorbent cores comprising two or more layers are also contemplated for the absorbent articles as disclosed herein.

An absorbent article as disclosed herein comprises an absorbent core being enclosed by a liquid-permeable core cover comprising an upper core cover layer and a lower core cover layer. The absorbent core has a pair of longitudinally extending side edges and a pair of transversely extending end edges. The core cover layers are connected by side seals extending along the side edges of the absorbent core. The absorbent core comprises one or more longitudinally extending channels, such as two channels, three channels, etc., arranged at a distance from the side seals, each of the one or more channels being free or substantially free from absorbent material and having a channel seal extending therein. The channel seal or channel seals join the upper and lower core cover layers of the core cover within the channel, with a seal strength of the channel seal being higher than a seal strength of each of the first and the second side seals of the absorbent core.

The absorbent article as disclosed herein may be varied within the scope of the appended claims. For example, the materials and dimensions used for the different layers forming an absorbent article as disclosed herein may be varied, as indicated above. The absorbent article may further include any useful component or feature as known in the art such as fluid acquisition and distribution components, leg elastics, standing gathers, crotch and waist elastics, side panels, fastening systems, wetness indicators, skin care agents, disposal means, etc., as known in the art and depending on the type of absorbent article intended.

DETAILED DESCRIPTION

Different aspects of the present disclosure will be described more fully hereinafter with reference to the enclosed drawings. The embodiments disclosed herein can be realized in many different forms and should not be construed as being limited to the aspects set forth herein. It is to be understood that although the absorbent article shown in the Figures is a pant-type article, the absorbent core as described in the examples may be used in any disposable absorbent article for absorbing urine, feces and/or vaginal discharges, as disclosed herein.

The drawings are schematic and individual components, such as layers of material are not necessarily drawn to scale. The pant-type article which is shown in the figures is a simplified article, and the article may contain further features, such as barrier cuffs. It is also to be understood that the waist elastic disclosed herein is optional or any other suitable type of waist elastic may be used. The side seams may be reclosable side seams, and the pant-type article may be provided with fastener elements to provide reclosability of the side seams.

Figure 1:
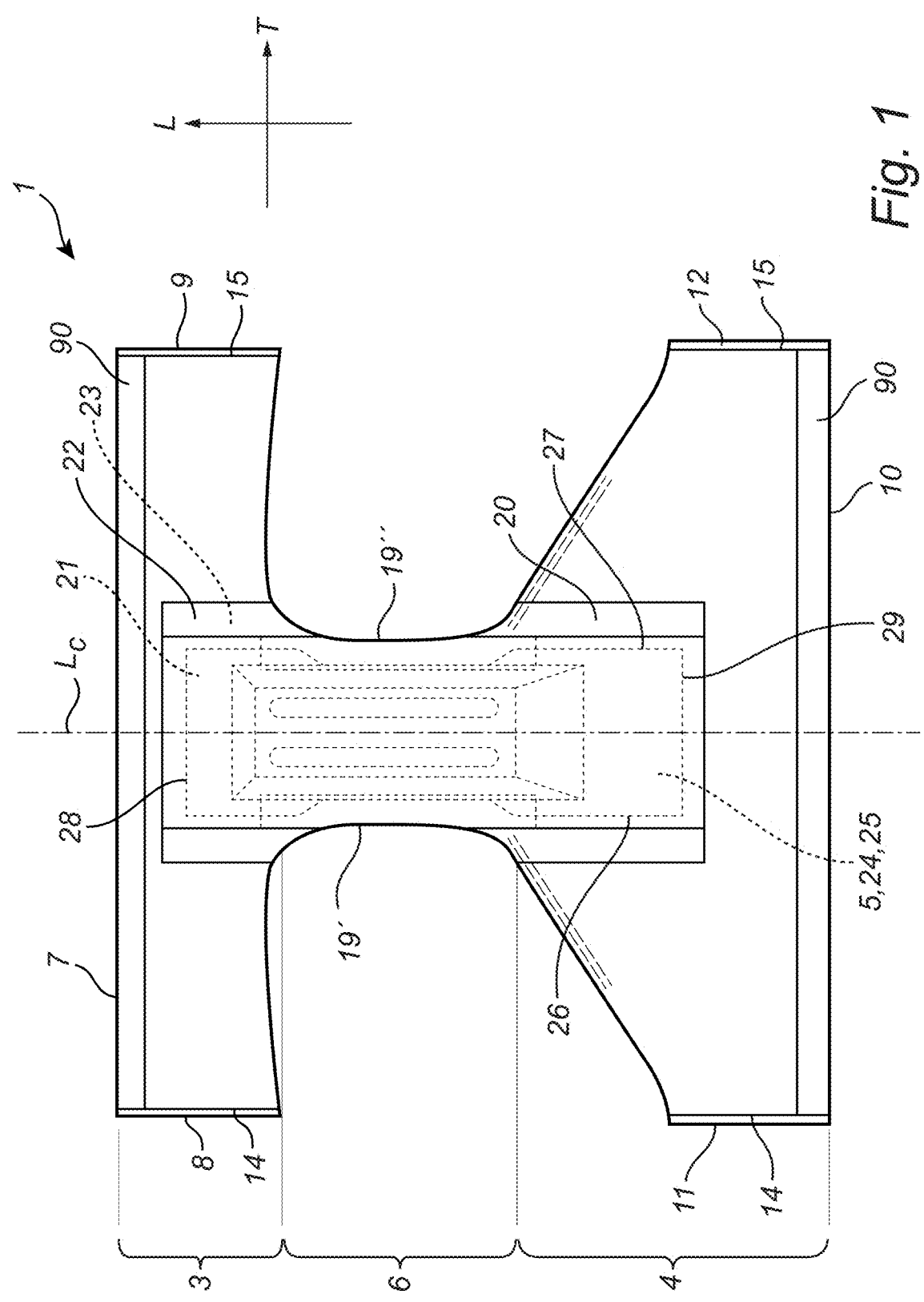
FIG. 1 shows a planar view of a stretched-out absorbent pant-type article with an absorbent assembly and with open side seams, as seen from an inner surface of the pant-type article.

With initial reference to FIG. 1, there is shown a pant-type article 1 in the form of a pant-type incontinence article for adult users. The pant-type article 1 is shown in FIG. 1 in an unfolded and flat condition with all elastic elements in a fully extended state. The pant-type article has a longitudinal direction L and a transverse direction T, perpendicular to the longitudinal direction with a longitudinal centerline Lc extending in the longitudinal direction L.

The pant-type article 1 is seen from the inner surface which is the surface which will be facing a wearer's body when the article is being worn and which is opposite the outer, garment-facing surface of the pant-type article 1.

The pant-type article 1 comprises a front portion 3, a rear portion 4 and an absorbent assembly 20 located in a crotch portion 6 of the pant-type article 1 and extending in the longitudinal direction L forward in over the front portion 3 and rearward in over the rear portion 4. The absorbent assembly 20 extends in the longitudinal direction L from the front portion 3 through the crotch portion 6 and into the rear portion 4. The absorbent assembly 20 in the pant-type article shown in the figures is a separately produced component which comprises an absorbent core 21 which is enclosed between an upper core cover layer 24 and a lower core cover layer 25 of a core cover 5 and which is further enclosed between a liquid permeable topsheet 22 and a liquid barrier layer 23. The absorbent core 21 is arranged between the topsheet 22 and the liquid barrier layer 23 with the upper core cover layer 24 facing the liquid topsheet 22 and the lower core cover layer 25 facing the liquid barrier layer 23.

As disclosed herein, the provision of an absorbent core 21 is not limited to absorbent articles having the absorbent core applied to the article as a component of a pre-fabricated absorbent assembly which already comprises a topsheet and a liquid barrier layer.

The front portion 3 has a front waist edge 7 extending in the transverse direction T and a pair of front side edges 8,9 extending in the longitudinal direction L. The rear portion 4 has a rear waist edge 10 extending in the transverse direction T and a pair of rear side edges 11, 12 extending in the longitudinal direction L.

Figure 4:
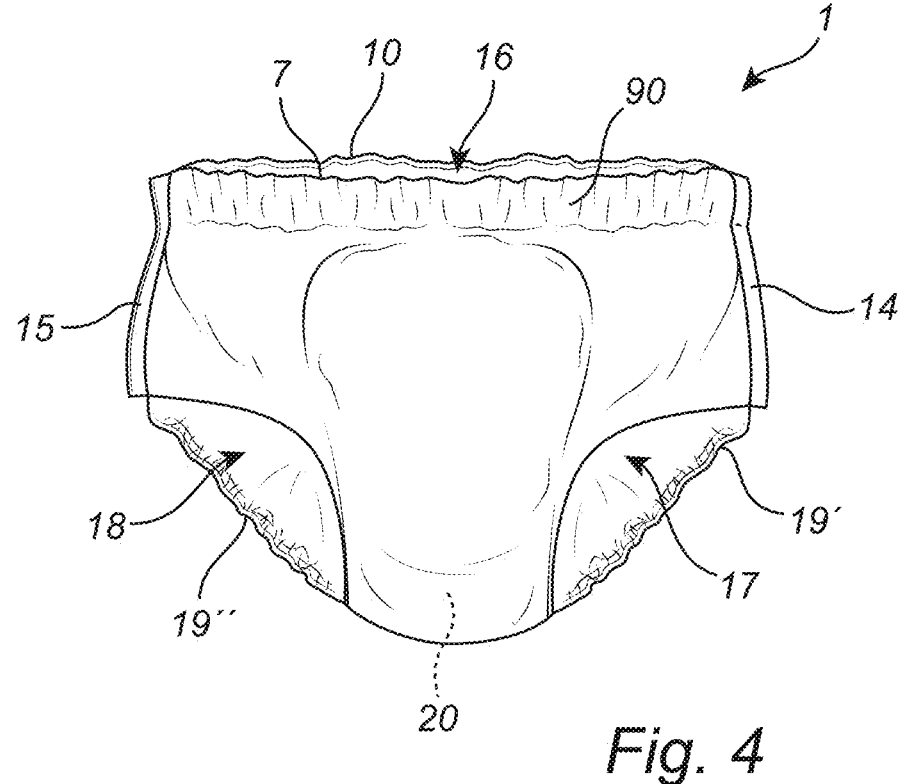
FIG. 4 shows the pant-type article in FIG. 1 with the side seams closed and in a non-stretched out condition, as it appears before use.

The first front side edge 8 is joined to the first rear side edge 11 in a first side seam 14 and the second front side edge 9 is joined to the second rear side edge 12 in a second side seam 15 to create the pant-type article 1 having a waist opening 16, a first leg opening 17 and a second leg opening 18, as shown in FIG. 4.

The side seams 14, 15 of the pant-type article 1 may be generally band-shaped joins which are formed by ultrasonic welding or thermowelding. To have sufficient strength to withstand the forces to which the pant-type article 1 is exposed during donning of the article and to allow sufficient production tolerances, the side seams commonly have a width in the order of 5 to 10 millimeters. It is also known to make side seams having a width less than 5 mm.

It is generally desired that a soiled pant-type article can be easily removed without having to pull the article down over the legs of a user. Therefore, the side seams are commonly made such that they are breakable by manual force to allow a user or a caregiver to pull apart the side seams before removing a soiled pant-type article.

The waist opening 16 is defined by the front panel waist edge 7 and the rear panel waist edge 10. A first leg edge 19' defines the first leg opening 17 and a second leg edge 19" defines the second leg opening 18.

Figure 2:
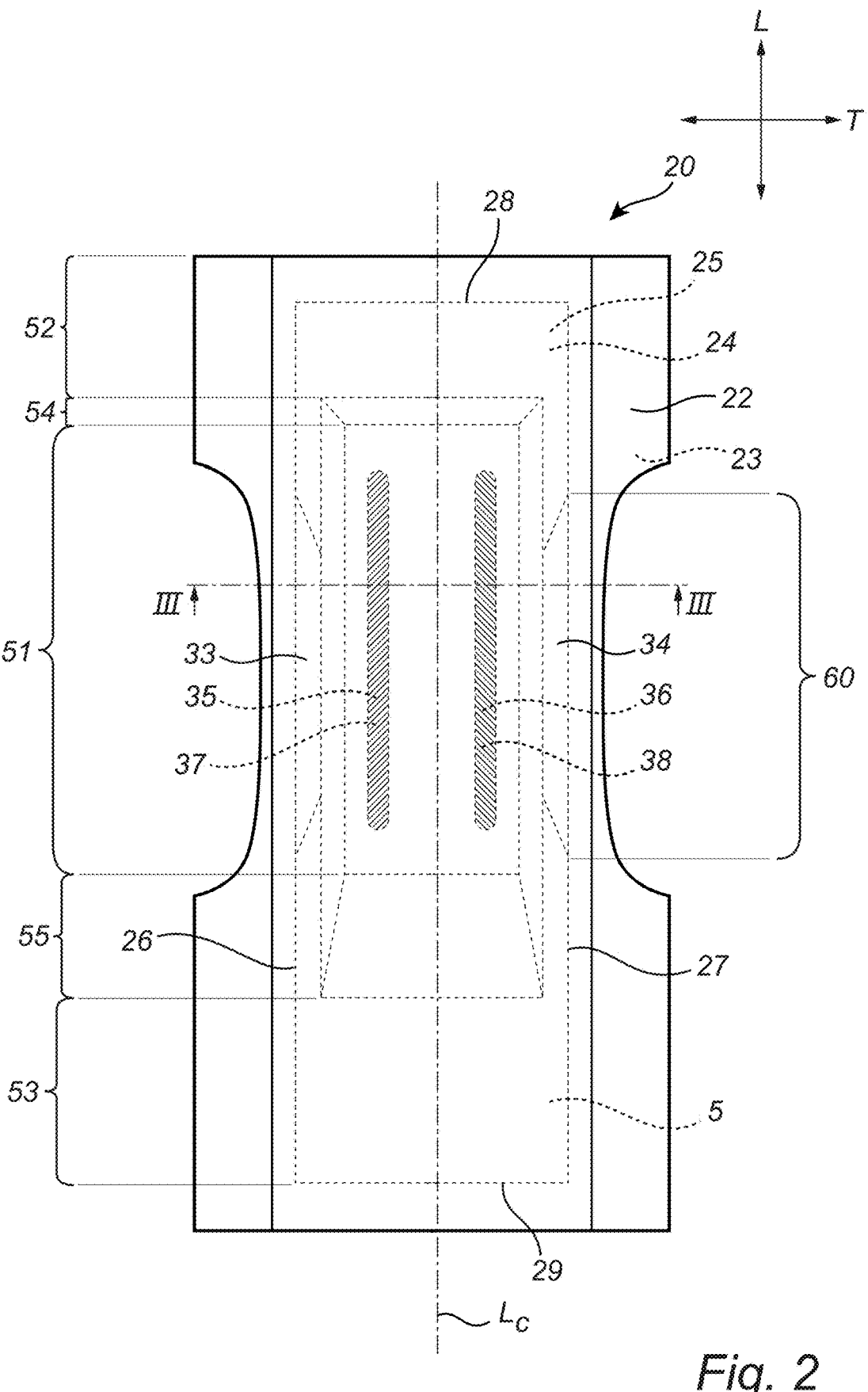
FIG. 2 shows an enlarged view of the absorbent assembly in the pant-type article in FIG. 1 with an absorbent core enclosed in a core cover.

With reference to FIG. 2, the absorbent core 21 has an hourglass shape with a first side edge 26 and a second side edge 27, a first end edge 28 and a second end edge 29. The first side edge 26 and the second side edge 27 of the absorbent core 21 have a main extension in the longitudinal direction L and the first end edge 28 and the second end edge 29 have a main extension in the transverse direction T.

A first channel 35 and a second channel 36 are arranged in the absorbent core 21 and extend in the longitudinal direction L on either side of the longitudinal center line Lc and at a distance from each of the first and second side edges 26,27 of the absorbent core 21. The channels 35,36 are free or substantially free from absorbent material.

The upper core cover layer 24 and the lower core cover layer 25 are connected to each other by a first side seal 33 extending along the first side edge 26 of the absorbent core 21 and by a second side seal 34 extending along the second side edge 27 of the absorbent core 21. In addition, the upper and lower core cover layers 24, 25 are connected by a first channel seal 37 extending in the first channel 35 and by a second channel seal 38 extending in the second channel 36.

As disclosed herein, the seal strength of the first and second channel seals 37,38 is higher than the seal strength of the first and second side seals 33,34 of the absorbent core 21. The seal strength of the first and second channel seals 37,38 may be 2.5 N/25 millimeter or more and the seal strength of the first and the second side seals 33,34 may be 2.0 N/25 millimeter or less.

At least a major part of the channel seals 37,38 are permanent seals which do not break under normal use and handling of the absorbent article. Accordingly, the channel seals 37,38 remain intact or substantially intact even after the absorbent article has absorbed liquid. The side seals 33,34 are breakable seals with low seal strength such that the side seals 33,34 break under influence of the forces exerted of the side seals 33, 34 as the absorbent material in the absorbent core 21 absorbs fluid and expands. The permanent or substantially permanent channel seals 37,38 restrict swelling in the thickness direction of the absorbent article 1, while the breakable side seals 33,34 allow the absorbent material to expand in the lateral or transverse direction. Thus, in the region of the absorbent core 21 where the channels 35,36 are arranged, the combination of permanent or substantially permanent channel seals 37,38 and breakable side seals 33,34 causes the absorbent core 21 to expand predominantly in the transverse direction T.

As disclosed herein, the breakable side seals 33, 34 and the channel seals 37,38 may be adhesive seals. However, weld seals or combinations of adhesive seals and weld seals are also contemplated for the core cover seals 33,34,37,38.

The upper and lower core cover layers 24, 25 may be formed from a single continuous cover material which is wrapped around the absorbent core 21. In the pant-type absorbent article which is shown in the figures, the upper and lower core cover layers 24,25 are formed from separate webs of material with the absorbent core 21 sandwiched between the core cover layers 24,25.

Depending on the type and size of absorbent article in which the one or more channels as disclosed herein are arranged, the length of the channels may range from 50 millimeter to 500 millimeter.

In a pant-type absorbent article for incontinent adult users, such as the absorbent article 1 shown in the figures, the channels 35,36 are preferably arranged in the crotch portion 6 of the article which is the narrow portion of the article which will be placed in the crotch of a user when the article is worn. The narrow crotch portion 6 of an absorbent article is the portion of the article which will receive a major part of excreted body fluid, such as urine. The crotch portion 6 must therefore have good absorption properties in terms of liquid acquisition, liquid distribution, and absorption capacity. The channels 35,36 in the absorbent core 21 contribute to rapid liquid acquisition and promote fluid distribution by channeling the fluid flow towards the front and rear portions 3, 4 of the absorbent article 1. In the absorbent article 1 which is shown in the figures, the length of the channels 35,36 substantially corresponds to the length of the crotch portion 6 and may typically be in the order of from 100 millimeter to 250 millimeter.

In wearable incontinence articles such as open diapers and pant-type diapers, the channels will typically have a length in the order of from 30% to 50% of the total length of the absorbent core. In smaller absorbent articles such as incontinence shields and sanitary napkins, the channels may extend almost to the ends of the absorbent core, such as up to 80% of the total length of the absorbent core.

In order to enhance the absorbent capacity in the narrow crotch portion 6 of the absorbent article 1, a central part 51 of the absorbent core 21 which arranged between a first end part 52 of the absorbent core 21 and a second end part 53 of the absorbent core 21, as seen in the longitudinal direction L, has a greater thickness than the end parts 52,53. In the absorbent article 1 shown in the figures, the first end part 52 is the front end part 52 of the absorbent core 21 and the second end part 53 is the rear end part 53 of the absorbent core 21.

The central part 51 of the absorbent core 21 has a uniform thickness and each of the first end part 52 and the second end part 53 of the absorbent core 21 has a uniform thickness, the central part 51 of the absorbent core 21 being delimited from each of the first end part 52 and the second end part 53 by a corresponding first transition zone 54 and a second transition zone 55. The thickness of the absorbent core 21 diminishes linearly from the central part 51 of the absorbent core 21 to the end parts 52,53 of the absorbent core 21 within the transition zones 54,55. The rear end part 53 has a greater extension in the longitudinal direction of the absorbent article 1 than the front end part 52. In the absorbent core 21 shown in FIG. 2, the rear transition zone 55 has a greater extension in the longitudinal direction L of the absorbent article 1 than the front transition zone 54.

However, the transition zones may have an equal extension in the longitudinal direction of the absorbent article or the front transition zone may be longer than the rear transition zone. Absorbent cores with a thickened central portion and thinner end portions but without transition zones between the different portions of the cores are also contemplated for the absorbent articles as disclosed herein.

Moreover, the central portion and the end portions may have non-uniform thickness.

The ratio between the thickness of the central part 51 of the absorbent core 21 and the thickness of the front end part 52 may be in the range of from 4 to 1.5 and the ratio between the thickness of the central part 51 of the absorbent core 21 and the thickness of the second end part 53 may be in the range of from 4 to 1.5. The thinner end parts 52, 53 may have the same thickness or may have different thicknesses.

Furthermore, it is to be understood that a three-dimensional shape of the absorbent core is optional to the absorbent articles as disclosed herein and that the absorbent core may be planar or substantially planar. In a planar or substantially planar absorbent core, the absorbent capacity in the absorbent core may be different in different parts of the core as a result of different amounts of superabsorbent material being arranged in the different parts of the core.

The absorbent core 21 as disclosed herein may comprise any material suitable for absorbing discharged bodily wastes, such as cellulosic fluff pulp, tissue layers, highly absorbent polymers (super absorbents), absorbent foam materials including hydrogel-foam material, absorbent nonwoven materials, or the like. The absorbent core can comprise non-absorbent components such as stiffening elements, shaping elements, binders, etc. Various types of liquid-receiving and liquid distribution elements can also be included in the core.

The absorbent core 21 preferably comprises superabsorbent material in an amount of from 5% by weight to 80% by weight of superabsorbent material, such as from 30% by weight to 80% by weight of superabsorbent material, at least in the central part 51 of the absorbent core 21. As set out herein, the superabsorbent content may be lower in the front end part 52 and/or in the rear end part 53 of the absorbent core than in the central part 51 of the absorbent core 21 or may be the same in all parts of the absorbent core 21.

The superabsorbent material is a polymeric material and may be in the form of particles, granules fibers, flakes, etc.

As disclosed herein, the absorbent core 21 may comprise a mixture of absorbent cellulose fibers, such as cellulose pulp fibers, and superabsorbent material.

A high amount of superabsorbent material in the absorbent core, makes it possible to produce absorbent articles which are thin and discrete while offering high absorbent capacity and an ability to chemically bind and immobilize absorbed fluid which results in an absorbent article having high leakage security and a dry inner surface even after having absorbed a large amount of fluid.

The superabsorbent material absorbs liquid upon swelling and formation of an aqueous gel. In order to fully utilize the absorbent capacity of the superabsorbent material, the absorbent article must provide sufficient expansion room for the superabsorbent material. As the absorbent core is enclosed in the core cover 5, the swelling superabsorbent material will exert pressure on the core cover. In the central part 51 of the absorbent core 21 where the channels 35,36 with the permanent channel seals 37,38 are arranged, the swelling room is restricted in the area between the channels 35,36 causing this area to grow somewhat thicker and stiffer until the core cover prohibits further swelling.

The absorbent core 21 has an hourglass shape with the distance between the side edges 26,27 of the absorbent core 21 being greater at the end edges 28, 29 of the absorbent core 21 than in an intermediate region 60 of the absorbent core 21 where the absorbent core has a smaller width than at the end edges 28, 29.

Figure 3A:
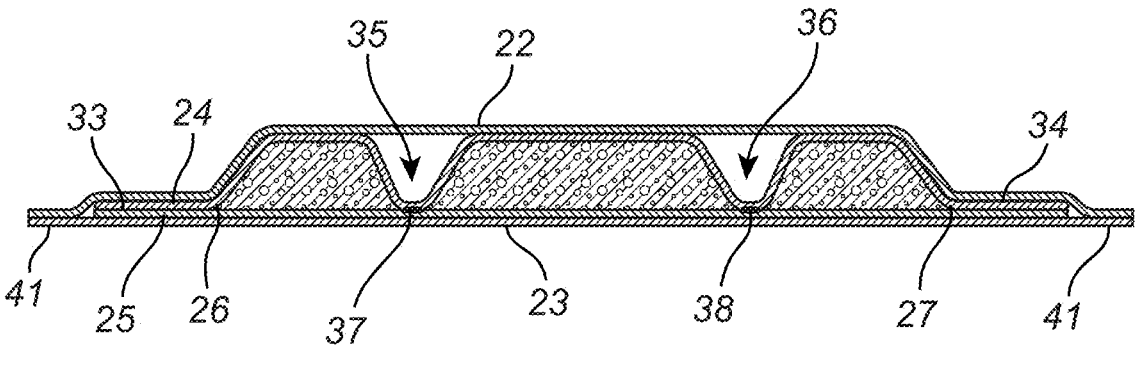
FIG. 3a shows a cross section through the absorbent assembly in FIG. 2, taken along the line III-III when the absorbent core is in a dry state.
Figure 3B:
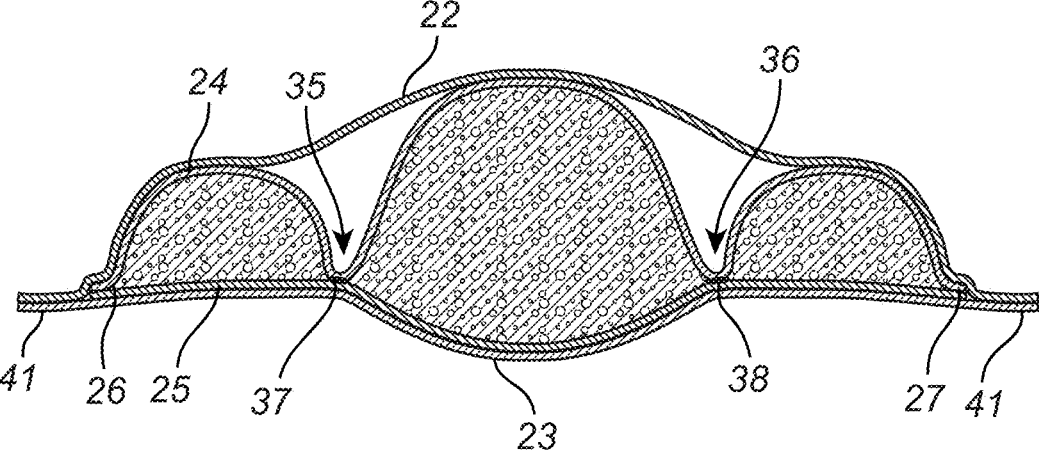
FIG. 3b shows a cross section through the absorbent assembly in FIG. 2, taken along the line III-III when the absorbent core is in a wet state.

FIGS. 3a and 3b show a cross section taken along the line III-III through the absorbent core 21 in FIG. 2. FIG. 3a shows the absorbent core 21 in a dry state, before the absorbent core 21 has absorbed any liquid and FIG. 3b shows the absorbent core 21 in a wet state, after absorption and swelling of the absorbent core 21.

The absorbent core 21 is shown enclosed between the upper core cover layer 24 and the lower core cover layer 25 and between the liquid permeable topsheet 22 and the liquid barrier layer 23. The absorbent core 21 is arranged between the topsheet 22 and the liquid barrier layer 23 with the upper core cover layer 24 facing the liquid topsheet 22 and the lower core cover layer 25 facing the liquid barrier layer 23.

The topsheet 22 and the liquid barrier layer 23 extend beyond the periphery of the absorbent core 21 and are joined to each other in an edge seal 41 extending along the periphery of the absorbent core outward of the side edges 26, 27 and the end edges 28, 29 of the absorbent core 21. The edge seal 41 between the topsheet 22 and the liquid barrier layer 23 is preferably a permanent seal.

As the absorbent core 21 absorbs body fluid, the absorbent material in the absorbent core 21 swells causing the portion of the absorbent core 21 which is located between the channels 35,36, and which is confined between the permanent channel seals 37,38, to assume a sausage-like shape with the absorbent material completely filling the available space between the channels 35, 36 and causing the topsheet 22 and the upper core cover layer 24 to bulge upwards and the liquid barrier layer 23 and the lower core cover layer 25 to bulge downwards, as shown in FIG. 3b. The absorbent material which is arranged in the portions of the absorbent core 21 which are located between the channels 35,36 with the permanent channel seals 37,38 exerts pressure on the breakable side seals 33,34 causing the side seals 33,34 to rupture and to provide lateral expansion room for the absorbent material. In this way, the absorbent core may absorb liquid and swell while the side edges 26, 27 of the absorbent core 21 remain soft and comfortable. As can be deduced from FIGS. 3a and 3b, the lateral swelling of the absorbent core 21, causes the side edges 26, 27 of the absorbent core to move outward in the transverse direction T, whereby the hourglass shape of the absorbent core becomes gradually obliterated.

As set out herein, the channel seals 37, 38 may be breakable seals at the ends of the channels 35, 36, where the absorbent core 21 has a somewhat greater width than in an intermediate part of the channels 35, 36 where it is desirable to control the direction of swelling such that the portions of the absorbent core 21 which are located along the side edges 26, 27 expand predominantly in the transverse direction of the absorbent core 21, as shown in FIG. 3b.

The liquid permeable topsheet 22 may comprise or consist of a nonwoven material. Other suitable topsheet materials include tow fibers, porous foams, apertured plastic films and laminates and combinations of such materials. The materials which are best suited as topsheet materials are soft and non-irritating to the skin, are readily penetrated by body fluids, and display low rewet.

The liquid barrier layer 23 may consist of a thin plastic film, e. g. a polyethylene or polypropylene film, a nonwoven material coated with a liquid impervious material, a hydrophobic nonwoven material which resists liquid penetration or laminates of plastic film and nonwoven. The liquid barrier layer material may be breathable to allow vapour to escape from the absorbent body, while still preventing liquids from passing through the liquid barrier layer material.

The topsheet and liquid barrier layer may be connected to each other for example by adhesive bonding, gluing or welding by heat or ultrasonically. The topsheet and/or the liquid barrier layer may further be attached to the core cover by any method known in the art, such as adhesive, heat-bonding, welding, etc.

A pant-type articles as disclosed herein may have a two-part chassis with a crotch panel which is connected to a front panel along a front panel crotch edge, and which is connected to a rear panel along a rear panel crotch edge. The front and rear panels may be made from elastic or elasticized web material or an elastic laminate material, and the crotch panel may be a non-elastic web material or a non-elastic laminate material. Alternatively, the pant-type article may have a unitary chassis having a non-elastic outer or inner cover web extending the full distance between the front panel waist edge and the rear panel waist edge, the cover web constituting a non-elastic layer of each of the front panel and the rear panel and constituting the crotch web material in the crotch region of the pant-type article.

An elastically stretchable front body panel and an elastically stretchable rear body panel may comprise or consist of a stretchbonded laminated elastic web material.

Suitable stretch-bonded laminates may comprise nonwoven material layers or webs such as spunbond, air laid, wet laid, carded, electro spun or meltblown nonwovens. The nonwoven material may be bonded by any suitable technique, such as by needling, hydroentangling, ultrasonic welding, or thermobonding.

The fibers of the nonwoven materials used herein may be man-made fibers, natural fibers or mixtures of man-made and natural fibers. Man-made fibers include mono-component, bi-component and multicomponent fibers of polymers such as polyolefins, polyesters, polyacrylates, etc., as well as regenerated fibers such as viscose fibers and modal fibers. Natural fibers are for instance cellulosic fibers such as pulp fibers, cotton fibers, flax, hemp, etc.

The pant-type article 1 as disclosed herein may have an elastic waist feature 90 arranged along the waist opening 16. An elastic waist feature 90 may be formed by one or more elastic elements extending parallel with the front panel waist edge 7 and the rear panel waist edge 10. The elastic waist element or elements may be incorporated in the front portion 3 and the rear portion 4 or may be applied as a separate waistband which is attached to the front panel waist edge 7 and the rear panel waist edge 10. The pant-type article 1 which is shown in the Figures has an elastic waist feature 90 which extends around the full circumference of the waist opening 16. However, an elastic waist feature may be arranged only along a part of the waist opening, such as only along the rear waist edge, only along the front waist edge or along a part of one or both the front and the rear waist edge which part has a length which is less than the full length of the corresponding waist edge. The elastic material in elastic elements arranged along the leg openings 17,18 and the waist opening 16 as disclosed herein may be any suitable elastic material such as natural or synthetic rubber, thermoplastic elastomers, such as thermoplastic polyurethane or styrene block co-polymers or elastane, also referred as to spandex (polyurethane-polyurea copolymer). The elastic elements may be of the elastane type that is available under the trade name "LYCRA", but any suitable elastic thread may be used.

The nonwoven web-materials used in the absorbent articles as disclosed herein may comprise thermoplastic material. The nonwoven web-materials will typically be incorporated in joins and seams in the absorbent article and it may be desirable that the nonwoven webs be weldable by heat or by ultrasonic welding processes.

Examples of suitable polymers for use in the fibrous nonwoven webs as disclosed herein are polyethylene polypropylene and other polyolefin homopolymers and copolymers and polyesters. The weldable nonwoven webs have a high content of thermoplastic component and preferably contain at least 50% thermoplastic fibers and more preferably at least 80% thermoplastic fibers.

Test Methods

Test Method for Measuring Seal Strength

At least 10 days must pass between article manufacturing and the occasion for seal strength measurement.

The core with enclosing cover layers is carefully separated from other components of the absorbent article. If the lower core cover layer cannot be separated from the backsheet of the absorbent article without damaging the lower core cover layer, the backsheet should be left attached to the lower core cover layer when carrying out the seal strength test.

The exposed core with the core cover layers is placed flat on a support surface. If elastic is present in the core, the core should be stretched out and fixed in place on the support surface using strips of tape, mechanical fasteners, or similar.

Rectangular samples, 25 mm wide, are punched out from the core, each sample including a portion of the seal to be tested. The samples are punched out with the width direction of each sample parallel to the longitudinal centerline of the core and with the length direction of each sample perpendicular to the longitudinal centerline of the core. The samples are punched out such that the seal extends across an outer end of the sample, with inner end portions of the upper and lower core cover layers forming cover flaps extending towards the longitudinal centerline of the article. Any loose absorbent material between the core cover flaps is removed. The core cover flaps may be extended and/or reinforced with high friction tape, to ensure a stable and slip free attachment in the tensile tester clamps. It is of importance that the longitudinal edges of the test pieces are even and without break notches.

The samples are punched immediately adjacent one another. For example, from a seal having a length of 210 mm, eight 25 mm wide test samples may be punched out, with 10 mm of the seal remaining at one end of the seal and not being used for testing.

The samples, prepared as described above, are conditioned for 24 hours in a controlled environment with the temperature set to 23° C.+/−1° C. and 50%+/−5% relative humidity. Testing is performed in this same environment.

The samples are tested in a conventional tensile tester, such as available from Lloyd Instruments or the Instron Corporation.

Figure 5:
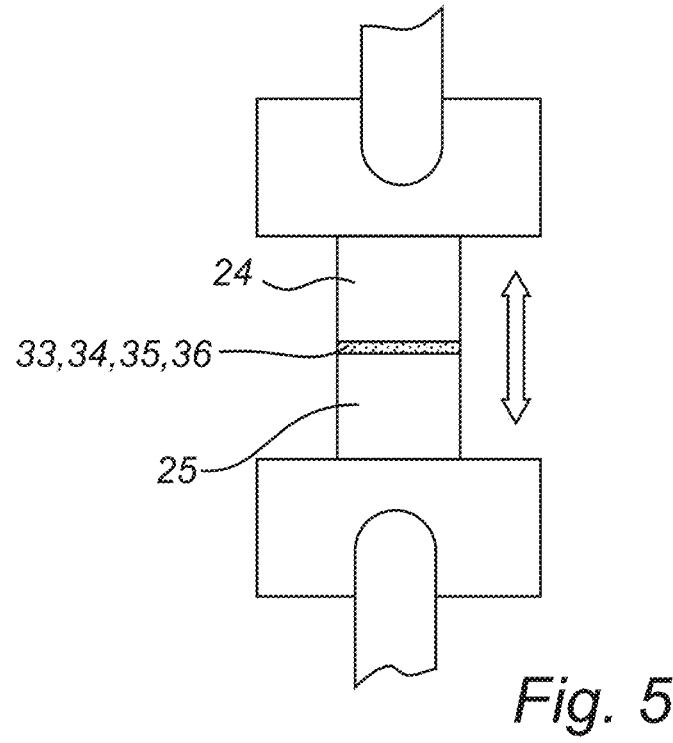
FIG. 5 shows how the test pieces are mounted in the clamps of the test instrument.
Figure 6:
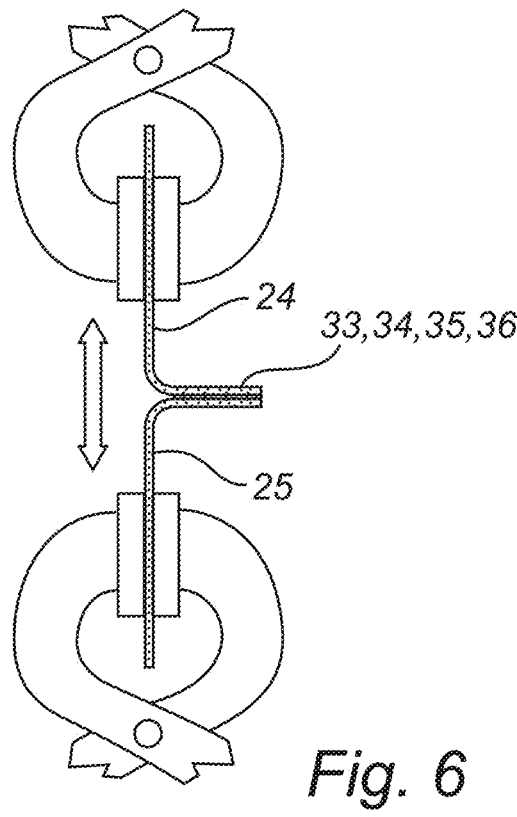
FIG. 6 shows how the test pieces are mounted in the clamps of the test instrument.

The core cover flaps are inserted vertically into the clamps of the tensile tester. The clamps should be as wide or wider than the sample. At insertion, tension over the seal should be avoided, but also excessive slack in the tested sample. The upper crosshead of the instrument is then set to move at a constant speed of 300 mm/min until the upper core cover layer separates from the lower core cover layer along the tested seal. The measured maximum force is registered in Newtons/25 mm (N/25 mm). FIGS. 5 and 6 illustrate how the test pieces are mounted in the clamps of the test instrument.

The seal strength of the tested seal is the arithmetic mean value based on all individual samples that can be cut along the seal. For example, the strength of the 210 mm long seal as set out above, is the mean value of the seal strengths obtained from the testing of the eight test pieces which were punched out along the seal.

The invention claimed is:

1. An absorbent article comprising an absorbent core, the absorbent core comprising absorbent material, the absorbent core being enclosed by a liquid-permeable core cover, the core cover comprising an upper core cover layer and a lower core cover layer, the absorbent article and the absorbent core having a longitudinal direction and a transverse direction perpendicular to the longitudinal direction, with a longitudinal center line extending in the longitudinal direction, the absorbent core having a first side edge and a second side edge, the first side edge and the second side edge of the absorbent core having a main extension in the longitudinal direction, and a first end edge and a second end edge, the first end edge and the second end edge having a main extension in the transverse direction, the upper core cover layer and the lower core cover layer being connected in a first side seal extending along the first side edge of the absorbent core and in a second side seal extending along the second side edge of the absorbent core, the absorbent core comprising one or more channels extending in the longitudinal direction at a distance from each of the first side seal and the second side seal, each of the one or more channels being free or substantially free from absorbent material and having a channel seal extending therein, the channel seal joining the upper and lower core cover layers of the core cover within the channel, wherein a seal strength of the channel seal is higher than a seal strength of each of the first and the second side seals of the absorbent core.

2. An absorbent article according to claim 1, wherein the seal strength of the channel seal or channel seals is 2.5 N/25 millimeter or more and the seal strength of the first and the second side seals is 2.0 N/25 millimeter or less.

3. An absorbent article according to claim 1- or 2, wherein the absorbent core has an hourglass shape or a T-shape in the plane defined by the longitudinal direction and the transverse direction.

4. An absorbent article according to claim 1, 2 or 3, wherein the side seals and the channel seal(s) are adhesive seals, weld seals or combinations of adhesive seals and weld seals.

5. An absorbent article according to claim 4, wherein the first side seal, the second side seal and each channel seal are adhesive seals.

6. An absorbent article according to claim 5, wherein a basis weight of adhesive in each channel seal is higher than a basis weight of adhesive in each of the first side seal and the second side seal.

7. An absorbent article according to claim 6, wherein the basis weight of adhesive in each channel seal is 3 g/m$^2$ or more and the basis weight of adhesive in each side seal is 5 g/m$^2$ or less.

8. An absorbent article according to claim 1, wherein the core cover, is formed from a single continuous cover material being wrapped around the absorbent core, the first side edge and the second side edge of the absorbent core being arranged inside a corresponding first side fold and a second side fold in the continuous cover material, the first and second side seals being arranged laterally inward of the corresponding first and second side folds.

9. An absorbent article according to claim 1, wherein the upper core cover layer and the lower core cover layer are separate core cover layers.

10. An absorbent article according to claim 1, wherein the absorbent article, in addition to the upper core cover layer and the lower core cover layer, comprises a liquid permeable topsheet and a liquid barrier layer, the absorbent core being arranged between the liquid permeable topsheet and the liquid barrier layer with the upper core cover layer facing the liquid permeable topsheet and the lower core cover layer facing the liquid barrier layer.

11. An absorbent article according to claim 1, wherein the absorbent core comprises super-absorbent material.

12. An absorbent article according to claim 1, wherein the one or more channels are constituted by two channels extending spaced apart and symmetrically arranged on each side of the longitudinal center line, between the longitudinal center line and a corresponding one of the first side seal and the second side seal.

13. An absorbent article according to claim 1, wherein the length of each of the one or more channels is in the range of from 50 millimeter to 500 millimeter.

14. An absorbent article according to claim 1, wherein the absorbent core comprises two or more parts having different absorption capacity.

15. An absorbent article according to claim 14, wherein a central part of the absorbent core-being arranged between a first end part of the absorbent core and a second end part of the absorbent core, as seen in the longitudinal direction, has a greater thickness than a thickness of the first end part and a greater thickness than a thickness of the second end part.

16. An absorbent article according to claim 15, wherein the central part of the absorbent core has a uniform thickness and each of the first end part and the second end part of the absorbent core has a uniform thickness, the central part of the absorbent core being delimited from each of the first end part and the second end part by a corresponding first transition zone and a second transition zone.

17. An absorbent article according to claim 16, wherein the first end part is a front end part and the first transition zone is a front transition zone having an extension in the longitudinal direction of from 5 millimeter to 30 millimeter and wherein the second end part is a rear end part and the second transition zone is a rear transition zone having an extension in the longitudinal direction of from 20 millimeter to 80 millimeter.

18. An absorbent article according to claim 16, wherein a ratio between the thickness of the central part of the absorbent core and the thickness of the first end part is in the range of from 4 to 1.5.

19. An absorbent article according to claim 16, wherein a ratio between the thickness of the central part of the absorbent core and the thickness of the second end part is in the range of from 4 to 1.5.

20. An absorbent article according to claim 1, wherein the absorbent core has a length being determined as the distance between a point on the first end edge where the first end edge intersects with the longitudinal center line and a point on the second end edge where the second end edge intersects with the longitudinal center line, the length of the absorbent core being in the range of from 300 millimeter to 700 millimeter.

21. An absorbent article according to claim 1, wherein the absorbent core comprises from 5% by weight to 80% by weight of superabsorbent material.

* * * * *